United States Patent
Ito et al.

(10) Patent No.: US 10,783,642 B2
(45) Date of Patent: Sep. 22, 2020

(54) ULTRASONIC DIAGNOSTIC APPARATUS AND ULTRASONIC IMAGE PROCESSING METHOD

(71) Applicant: Hitachi, Ltd., Chiyoda-ku, Tokyo (JP)

(72) Inventors: Takumi Ito, Tokyo (JP); Koji Waki, Tokyo (JP)

(73) Assignee: Hitachi, Ltd., Tokyo (JP)

(\*) Notice: Subject to any disclaimer, the term of this patent is extended or adjusted under 35 U.S.C. 154(b) by 69 days.

(21) Appl. No.: 16/361,763

(22) Filed: Mar. 22, 2019

(65) Prior Publication Data
US 2020/0043172 A1 Feb. 6, 2020

(30) Foreign Application Priority Data
Aug. 2, 2018 (JP) ................. 2018-145997

(51) Int. Cl.
| | |
|---|---|
| *G06T 7/11* | (2017.01) |
| *A61B 8/08* | (2006.01) |
| *A61B 8/00* | (2006.01) |
| *G06T 7/00* | (2017.01) |
| *G06T 7/12* | (2017.01) |
| *G06T 7/13* | (2017.01) |

(52) U.S. Cl.
CPC .............. *G06T 7/11* (2017.01); *A61B 8/0825* (2013.01); *A61B 8/465* (2013.01); *A61B 8/467* (2013.01); *A61B 8/5207* (2013.01); *G06T 7/0014* (2013.01); *G06T 7/12* (2017.01); *G06T 7/13* (2017.01); *G06T 2207/10132* (2013.01); *G06T 2207/30068* (2013.01)

(58) Field of Classification Search
CPC . G06T 7/11; G06T 7/0014; G06T 7/12; G06T 7/13; G06T 2207/30068; G06T 2207/10132; A61B 8/0825; A61B 8/467; A61B 8/465; A61B 8/5207; A61B 8/469
See application file for complete search history.

(56) References Cited

FOREIGN PATENT DOCUMENTS

| | | |
|---|---|---|
| JP | 8-131436 A | 5/1996 |
| JP | 2009-261493 A | 11/2009 |
| JP | 2010-259527 A | 11/2010 |
| JP | 2015-43911 A | 3/2015 |

*Primary Examiner* — Christopher Wait
(74) *Attorney, Agent, or Firm* — Crowell & Moring LLP

(57) ABSTRACT

A tomographic image includes a mammary gland image, a greater pectoral muscle image, and a boundary image. A plurality of search paths are set for the tomographic image. In each search path, a boundary search is executed from a deep spot toward a shallow spot. A region of interest is set so as to include the mammary gland image on the basis of a plurality of boundary points. An image portion in the region of interest is an image analysis target.

11 Claims, 14 Drawing Sheets

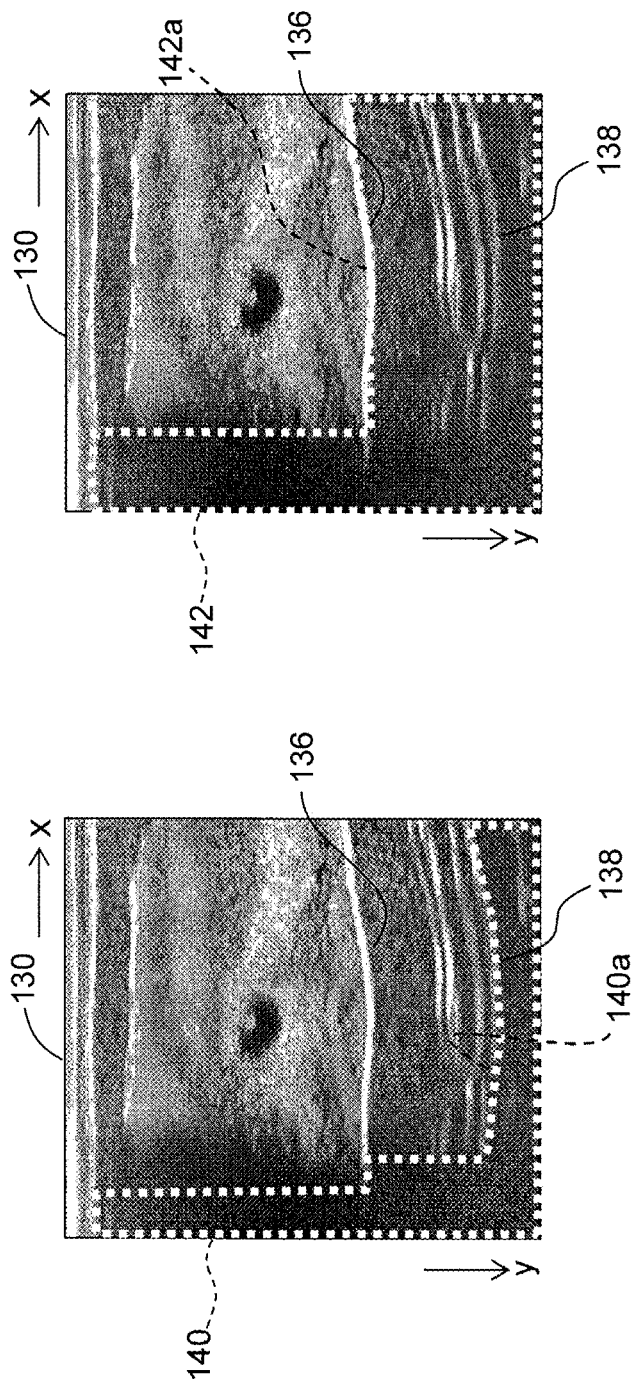

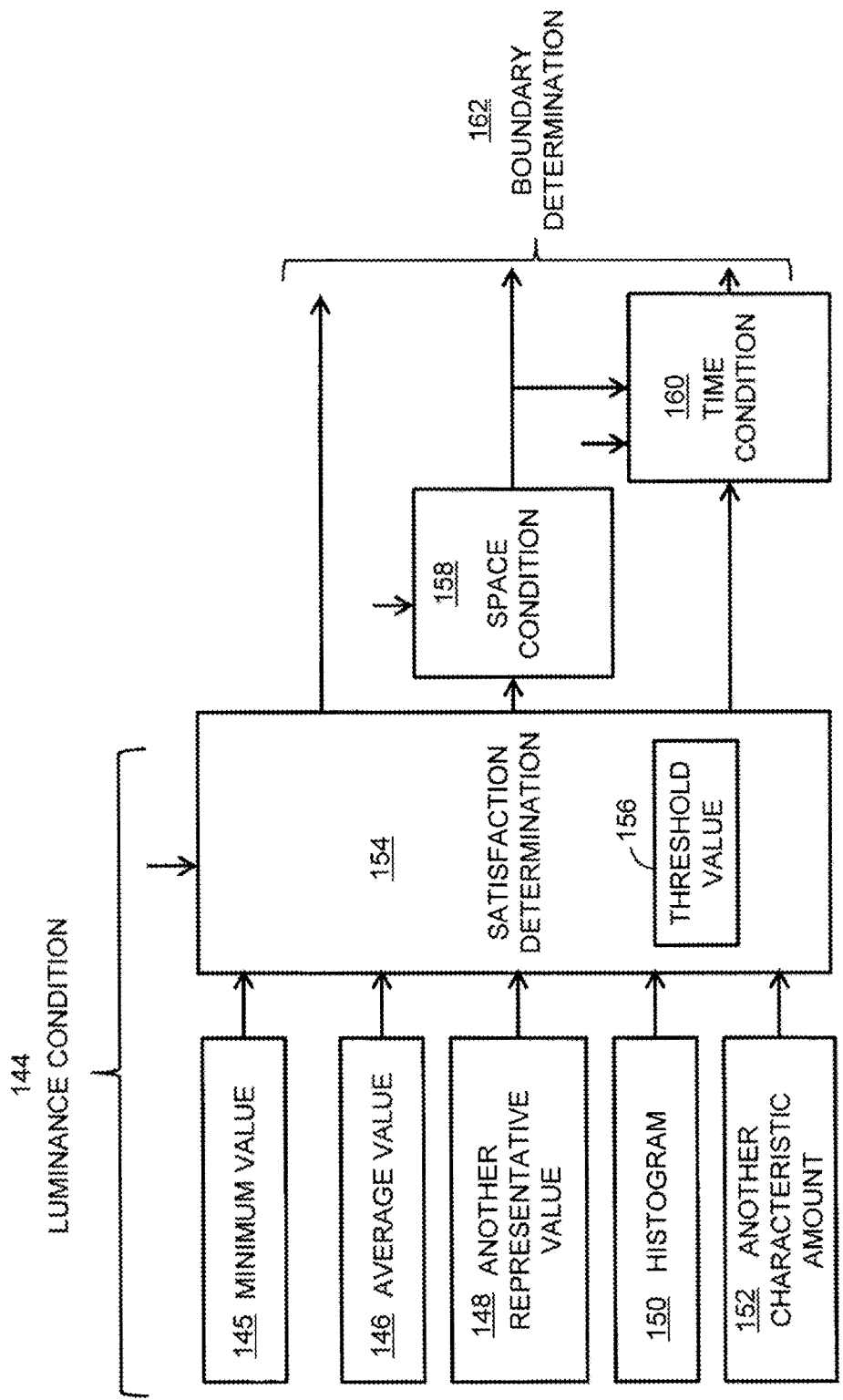

ULTRASONIC DIAGNOSTIC APPARATUS AND ULTRASONIC IMAGE PROCESSING METHOD

CROSS REFERENCE TO RELATED APPLICATION

This application claims priority to Japanese Patent Application No. 2018-145997 filed on Aug. 2, 2018, which is incorporated herein by reference in its entirety including the specification, claims, drawings, and abstract.

TECHNICAL FIELD

The present disclosure relates to an ultrasonic diagnostic apparatus and an ultrasonic image processing method, and more particularly, to generation of a region of interest.

BACKGROUND

An ultrasonic diagnostic apparatus is an apparatus that forms an ultrasonic image on the basis of a reception signal obtained by transmitting and receiving ultrasonic waves to and from a living body. A typical ultrasonic image is a tomographic image, which is an image showing a cross section of tissue. For example, in an examination of the breast, an ultrasonic probe is brought into contact with the breast surface, a tomographic image displayed by the contact is observed, and the presence or absence of a tumor in the mammary gland, an aspect of the tumor, or the like is diagnosed through the observation.

Recently, an ultrasonic diagnostic apparatus or an ultrasonic image processing apparatus equipped with a computer-aided diagnosis (CAD) function has been widely used. In such an apparatus, the CAD function is used for evaluation of an ultrasonic image or diagnosis. For example, in mammary gland diagnosis, a tomographic image is analyzed in real time using the CAD function. Specifically, a low-luminance tumor image (or low-luminance non-tumor) included in the tomographic image is automatically recognized and marked. As the CAD function, a grade of malignancy may be automatically determined for each tumor image.

For example, JP H08-131436 A discloses an ultrasonic diagnostic apparatus that automatically sets a region of interest according to a contour of a tissue. In addition, JP 2010-259527 A discloses a technology of performing a boundary search from a deep spot to a shallow spot on a plurality of search paths set on a tomographic image.

SUMMARY

On a tomographic image obtained by ultrasonic diagnosis of the breast, a greater pectoral muscle image appears at a deep spot in the tomographic image; specifically, below a mammary gland image, and it is easy for a low-luminance portion in the greater pectoral muscle image to be erroneously recognized and erroneously detected as a tumor image. Usually, a tumor occurs in the mammary gland, and thus, only the mammary gland image is an observation target. For this reason, it is conceivable to set a region of interest so as to include the mammary gland image present at a shallow spot and exclude the greater pectoral muscle image present at the deep spot, but manually setting the region of interest is cumbersome. A shadow (black region) may appear in the tomographic image due to a portion (for example, an end portion) of a transmission and reception surface of a probe floating from a body surface. It is desirable to determine the region of interest so that such a shadow is excluded from the region of interest, but manually setting the region of interest is still cumbersome.

Meanwhile, in the tomographic image obtained by the ultrasonic diagnosis of the breast, a boundary image flowing in a transverse direction relatively clearly appears between the mammary gland image and the greater pectoral muscle image. A portion on which an image analysis is to be performed in the tomographic image is usually a mammary gland image appearing above the boundary image. On the other hand, a region below the boundary image is a relative low-luminance region generally having uniformity. It is desirable to automatically generate regions of interest utilizing these properties or characteristics.

It is to be noted that there an image in which the properties or the characteristics described above are recognized among ultrasonic images obtained by ultrasonic diagnosis of tissues other than the breast, and it is also desirable to automatically generate a region of interest for such an image. Regarding the setting of the region of interest, JP H08-131436 A does not disclose using a boundary image flowing in a transverse direction. In addition, in the technology of JP 2010-259527 A, it is necessary to set the region of interest before setting the plurality of search paths.

An object of the present disclosure is to realize automatic generation of a region of interest suitable for a content of an ultrasonic image.

An ultrasonic diagnostic apparatus according to the present disclosure includes: a detecting unit that detects a plurality of boundary points by setting a plurality of search paths so as to traverse a plurality of positions in a boundary image on an ultrasonic image including the boundary image and performing a boundary search from a deep spot to a shallow spot on the plurality of search paths, the boundary image having a form which extends in a direction intersecting with a depth direction; and a generating unit that generates a region of interest including an attention tissue image present on a shallow side of the boundary image on the basis of the plurality of boundary points.

An ultrasonic image processing method according to the present disclosure includes: a generating step of generating a region of interest including an attention tissue image present on a shallow side of a boundary image on the basis of the boundary image, the boundary image having a form which extends in a direction intersecting with a depth direction on an ultrasonic image; and a displaying step of displaying an image representing the region of interest together with an image representing a result of an analysis performed on an image portion in the region of interest in the ultrasonic image or another ultrasonic image, wherein in the generating step, a boundary search from a deep spot to a shallow spot on the ultrasonic image is executed, and the region of interest is determined on the basis of a result of the boundary search.

A program according to the present disclosure is a program executed in an ultrasonic image processing apparatus, and includes: a function of detecting a plurality of boundary points by setting a plurality of search paths so as to traverse a plurality of positions in a boundary image on an ultrasonic image including the boundary image and performing a boundary search from a deep spot to a shallow spot on the plurality of search paths, the boundary image having a form in which the boundary image extends in a direction intersecting with a depth direction; and a function of generating a region of interest including an attention tissue image present on a shallow side of the boundary image on the basis of the plurality of boundary points.

According to the present disclosure, it is possible to realize automatic generation of a region of interest suitable for a content of an ultrasonic image.

BRIEF DESCRIPTION OF DRAWINGS

Embodiment(s) of the present disclosure will be described based on the following figures, wherein:

FIG. 13 is a view illustrating a processing result of the first example of the ultrasonic image processing method;

FIG. 14 is a view illustrating a processing result of the second example of the ultrasonic image processing method; and FIG. 15 is a diagram for describing a boundary determining method.

DESCRIPTION OF EMBODIMENTS

Figure 1:
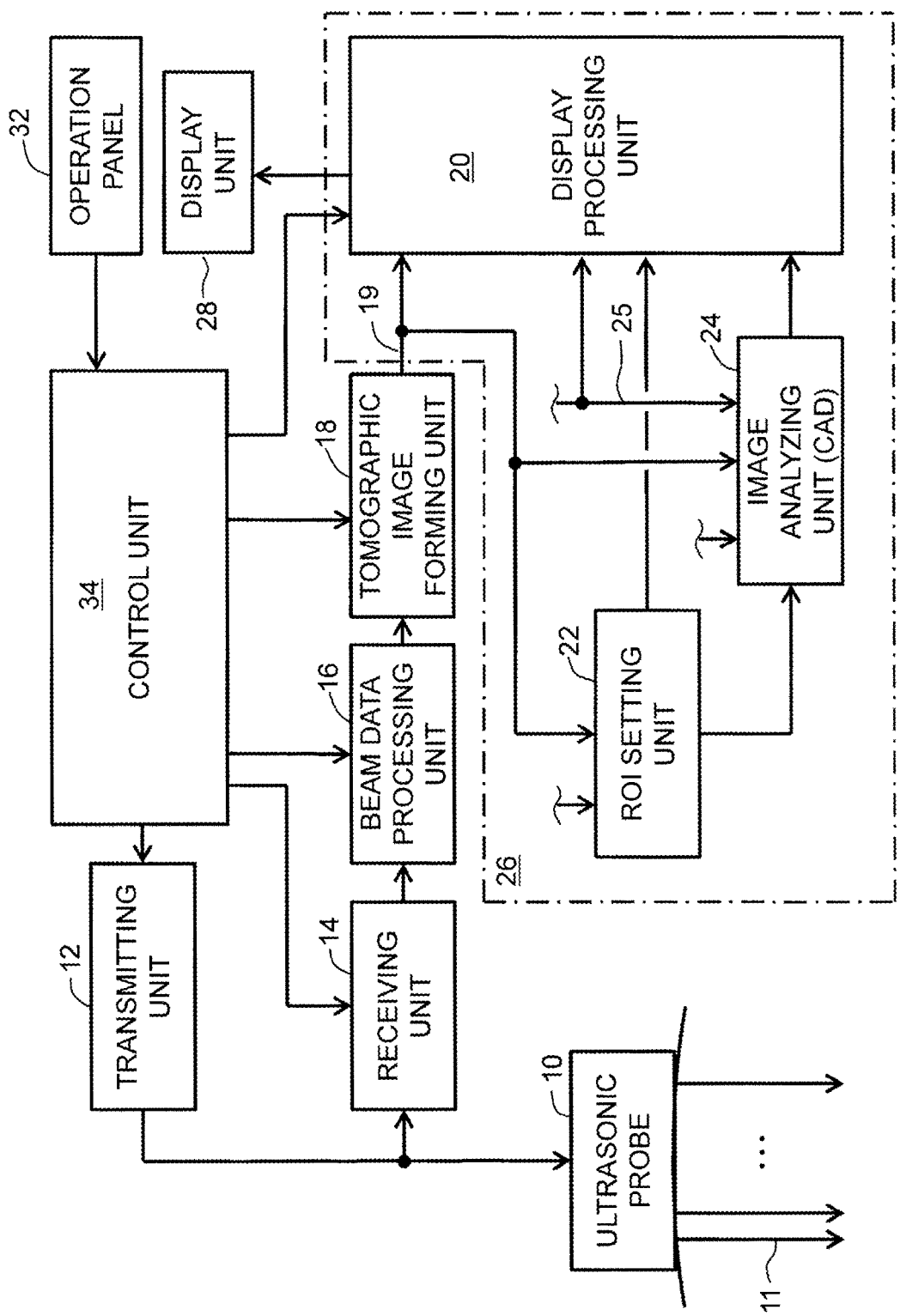
FIG. 1 is a block diagram illustrating an ultrasonic diagnostic apparatus according to an embodiment.

Hereinafter, embodiments of the disclosure will be described with reference to the drawings.

(1) Outline of Embodiment

An ultrasonic diagnostic apparatus according to an embodiment has a function of processing an ultrasonic image including a boundary image having a form which extends in a direction intersecting with a depth direction, and has a detecting unit and a generating unit in order to perform this processing. The detecting unit detects a plurality of boundary points by setting a plurality of search paths so as to traverse a plurality of positions in the boundary image, and performing a boundary search from a deep spot to a shallow spot on the plurality of search paths. The generating unit generates a region of interest including an attention tissue image present on a shallow side of the boundary image on the basis of the plurality of boundary points.

The above configuration is based on the premise that the boundary image relatively clearly appears in the ultrasonic image and that a region different from the boundary image spreads on a deep side of the boundary image, and sets a region of interest including an attention tissue image present on a front side of the boundary image using these properties or characteristics. The region of interest may be set to include the boundary image or may be set so as to exclude the boundary image. In a case where a shadow is generated in a portion of the ultrasonic image, the boundary image partially disappears in the shadow. In this case, since the boundary search proceeds up to the vicinity of the probe, the region of interest is set so as to avoid the shadow.

In the embodiment, the attention tissue image is a mammary gland image, and the boundary image is a boundary image between the mammary gland image and a greater pectoral muscle image present at a spot deeper than that of the mammary gland image. In the embodiment, the region of interest defines a portion that is an analysis target in the ultrasonic image or another ultrasonic image. The region of interest may be used for other purposes.

In the embodiment, a lower side of the region of interest is determined on the basis of a boundary point sequence including a plurality of boundary points, and a smoothing unit that spatially smooths the lower side is provided. According to this configuration, in a case where the lower side has a complicated form, the lower side can be smoothed. In addition, even when there is an erroneous recognition in detection of the plurality of boundary points, it is possible to mitigate an influence caused by the erroneous recognition. Further, in a case where the region of interest is displayed, an appearance of the region of interest can be improved. The boundary point sequence is smoothed, and as a result, the lower side may be smoothed, or the lower side itself may be smoothed.

In the embodiment, the smoothing unit further smooths the spatially smoothed lower side temporally. According to this configuration, in a case where a form of the lower side of the region of interest in a time axis direction is severely changed, the change can be suppressed. As a result, an accuracy of setting of the region of interest can be improved.

In the embodiment, the detecting unit detects each of the boundary points on the basis of satisfaction of a luminance condition on each of the search paths. Boundary detection is executed, for example, from the bottom to the top in units of echo data. In this case, reference may be made to one echo data, a plurality of echo data in a one-dimensional window, or a plurality of echo data in a two-dimensional window.

In the embodiment, the detecting unit detects each of the boundary points on the basis of continuous satisfaction of the luminance condition on each of the search paths. This configuration is based on the premise that the boundary image has a certain thickness, and according to this configuration, erroneous recognition of the boundary can be prevented or alleviated. For example, the boundary point may be detected on the basis of continuous satisfaction of the luminance condition n times on the search path. In this case, n may be adaptively set on the basis of a diagnostic range (diagnostic depth range) (here, n is an integer equal to or larger than 1). Since the thickness of the boundary image is changed depending on the diagnostic range, a value of n is adaptively set depending on such a change.

In the embodiment, the ultrasonic diagnostic apparatus includes a display unit that displays a region-of-interest image showing the region of interest together with the ultrasonic image. According to this configuration, it is possible to confirm that the attention tissue image is included in the region of interest. The region-of-interest image may be superimposed and displayed on the ultrasonic image, or the region-of-interest image and the ultrasonic image may be displayed in parallel with each other.

An ultrasonic image processing method according to an embodiment includes a generating step and a displaying step. In the generating step, a region of interest including an attention tissue image present on a shallow side of a boundary image is generated on the basis of the boundary image, the boundary image having a form which extends in a direction intersecting with a depth direction on an ultrasonic image. Specifically, in the generating step, a boundary search from a deep spot to a shallow spot on the ultrasonic image is executed, and the region of interest is determined on the basis of a result of the boundary search. In the displaying step, an image representing the region of interest is displayed together with an image representing a result of an analysis performed on an image portion in the region of interest in the ultrasonic image or another ultrasonic image.

A program according to an embodiment is a program executed in an ultrasonic image processing apparatus. Here, the ultrasonic image processing apparatus is a concept including an ultrasonic diagnostic apparatus, an information processing apparatus, and the like. The program is installed in the ultrasonic image processing apparatus through a portable storage medium or through a network.

(2) Details of Embodiment

In FIG. 1, a configuration of the ultrasonic diagnostic apparatus according to the embodiment is illustrated as a block diagram. The ultrasonic diagnostic apparatus is a medical apparatus that is installed in a medical institution such as a hospital and forms an ultrasonic image on the basis of reception data obtained by transmitting and receiving ultrasonic waves to and from a living body (subject to be examined). The ultrasonic diagnostic apparatus according to the embodiment has a function of automatically setting a region of interest (ROI) and a function (computer-aided diagnosis (CAD) function) of automatically analyzing the ultrasonic image, as described in detail below. In the embodiment, a tissue that is an ultrasonic diagnosis target is the breast; more particularly, the mammary gland. Another tissue may also be an ultrasonic diagnosis target.

An ultrasonic probe 10 functions as a unit for transmitting and receiving ultrasonic waves or a transducer. Upon ultrasonic diagnosis of the mammary gland, a transmission and reception surface (acoustic lens surface) of the ultrasonic probe 10 is brought into contact with the breast surface of the subject, and ultrasonic waves are transmitted and received to and from the breast surface in this state. The ultrasonic probe 10 includes a transducer element array including a plurality of transducer elements that are one-dimensionally arranged. An ultrasonic beam 11 is formed by the transducer element array, and a scanning plane is formed by electronic scanning of the ultrasonic beam 11. The scanning plane is an observation plane; that is, a two-dimensional data capturing region. As an electronic scanning manner of the ultrasonic beam, there are known an electronic sector scanning manner, an electronic linear scanning manner, and the like. Convex scanning of the ultrasonic beam may be performed. A two-dimensional (2D) transducer element array may be provided within the ultrasonic probe, and volume data may be acquired from the living body.

A transmitting unit 12 is a transmission beamformer that supplies a plurality of transmission signals in parallel to the plurality of transducer elements at the time of transmission, and is configured as an electronic circuit. A receiving unit 14 is a reception beamformer that performs phase alignment and summing (delay-and-sum) on a plurality of reception signals output in parallel from the plurality of transducer elements at the time of reception, and is configured as an electronic circuit. The receiving unit 14 includes a plurality of analog to digital (A/D) converters, a detection circuit, and the like. Beam data is generated by the phase alignment and summing of the plurality of reception signals in the receiving unit 14. In addition, a plurality of beam data arranged in an electronic scanning direction are generated per electronic scanning, and the plurality of beam data constitute reception frame data. Each beam data is constituted by a plurality of echo data arranged in a depth direction.

A beam data processing unit 16 is an electronic circuit that processes each beam data output from the receiving unit 14. The processing includes logarithmic transformation, correlation processing, and the like. The beam data having being processed is transmitted to a tomographic image forming unit 18.

The tomographic image forming unit 18 is an electronic circuit that forms a tomographic image (B mode tomographic image) on the basis of the reception frame data. The tomographic image forming unit 18 has a digital scan converter (DSC). The DSC has a coordinate conversion function, an interpolation function, a frame rate conversion function, and the like, and forms a tomographic image on the basis of a plurality of beam data arranged in a beam scanning direction. Data of the tomographic image is transmitted to a display processing unit 20 and an ROI setting unit 22.

It should be noted that an image processing module 26 is constituted by the display processing unit 20, the ROI setting unit 22, and an image analyzing unit 24. The image processing module 26 can be constituted by one or a plurality of processors operated according to a program. The image processing module 26 may be constructed in an information processing apparatus such as a personal computer (PC). In this case, the data of the tomographic image is transmitted from the ultrasonic diagnostic apparatus to the information processing apparatus. The information processing apparatus functions as an ultrasonic image processing apparatus.

The ROI setting unit 22 automatically generates an ROI (that is, a region of interest) on the basis of a tomographic image including a mammary gland image. In the embodiment, the ROI is generated in units of frames. The ROI may also be generated in units of a predetermined number of frames. The ROI setting unit 22 transmits coordinate information representing the generated ROI to the image analyzing unit 24. In addition, the ROI setting unit 22 generates an ROI image including the ROI as a frame and an internal image of the ROI, and transmits data of the ROI image to the display processing unit. Details of the ROI setting unit 22 will be described in detail below.

The image analyzing unit 24 functions as an image analysis means, and executes image analysis on an image portion included in the region of interest within the tomographic image. That is, the image analyzing unit 24 fulfills a CAD function. The image analyzing unit 24 performs the image analysis in units of frames. The image analysis may also be executed in units of a predetermined number of frames. The image analyzing unit 24 can be constituted by a machine learning analyzer such as a convolutional neural network (CNN). The image analyzing unit 24 has a function of recognizing, extracting, or discriminating a low-luminance tumor, a low-luminance non-tumor, or the like. The image analyzing unit 24 may have a function of evaluating a grade of malignancy of the tumor. In the embodiment, the image analyzing unit 24 analyzes the tomographic image to specify the tumor or the like, and generates a marker pointing to the tumor or the like. Data of the tomographic image (that is, an analysis result image) to which the marker is attached is transmitted to the display processing unit 20.

The display processing unit 20 has a graphic image generation function, a color calculation function, an image synthesis function, and the like. Specifically, the display processing unit 20 has a function of synthesizing the analysis result image and the ROI image in parallel to generate a display image. The analysis result image is an image in which marking is applied to a part found in the image analysis as described above. The ROI image is an image representing a form and a content of the ROI. The ROI image may be superimposed on the analysis result image or the tomographic image. The display image such as the tomographic image or the like is displayed on a display unit 28. The display unit 28 is constituted by a liquid crystal display (LCD), an organic electro-luminescence (EL) display device, or the like.

In the image analyzing unit 24, an elastic information image (elastography image) 25 may be analyzed. The elastic information image is an image showing tissue elasticity information calculated from tissue displacement. Even in this case, the ROI is set on the elastic information image, and an inner portion of the ROI is an analysis target. Another ultrasonic image may be the analysis target. It should be noted that the tomographic image after coordinate conversion is the analysis target in the embodiment, but frame data before the coordinate conversion may also be the analysis target. Since the frame data is also data representing a cross section of the tissue, the frame data can be included in the tomographic image in a broad sense.

A control unit 34 controls an operation of each component illustrated in FIG. 1. In the embodiment, the control unit 34 is configured by a CPU and a program. The control unit 34 may function as the image processing module 26. An operation panel 32 is an input device, which has a plurality of switches, a plurality of buttons, a trackball, a keyboard, and the like. It should be noted that ultrasonic image forming units other than the tomographic image forming unit 18 are not illustrated in FIG. 1. For example, an elastic information (elastography) image forming unit, a blood flow image forming unit, and the like may be provided.

Figure 2:
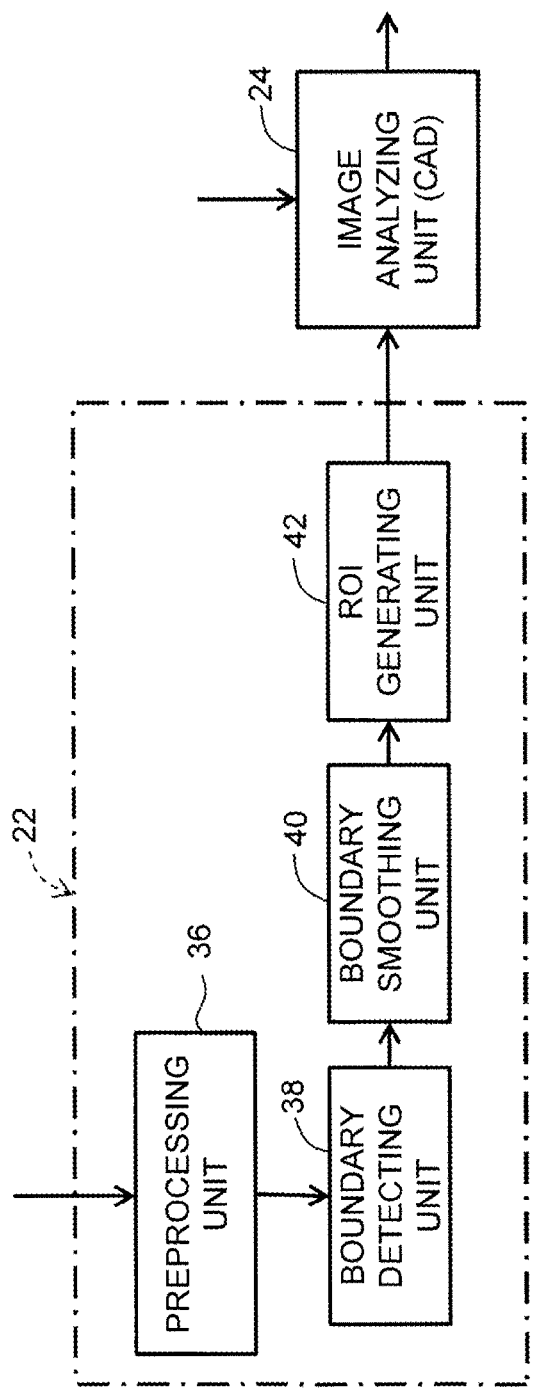
FIG. 2 is a block diagram illustrating a configuration example of a region of interest (ROI) setting unit.

FIG. 2 illustrates a configuration example of the ROI setting unit 22. The ROI setting unit 22 includes a preprocessing unit 36, a boundary detecting unit 38, and an ROI generating unit 42 in the illustrated example. The preprocessing unit 36 performs necessary preprocessing on the tomographic image. Examples of the preprocessing include smoothing processing, minimum value extraction processing, maximum value extraction processing, median (median extraction) processing, edge enhancement processing, and the like. Zero padding for arranging zeros outside the tomographic image for the purpose of boundary detection performed subsequently may be executed.

The boundary detecting unit 38 sets a plurality of search paths for the tomographic image and executes a boundary search on each search path, as described below. A start point of the boundary search is the deepest point on each search path in the embodiment, and the boundary search is sequentially executed from the start point toward a shallow side. In a tomographic image of the breast, usually, a boundary image clearly appears between a mammary gland image and a greater pectoral muscle image, and a rear side (deep side) of the boundary image is a low-luminance region generally having uniformity. The boundary search is sequentially executed from a deep spot to a shallow spot on the premise of these properties or characteristics. In addition, in the embodiment, an observation target is the mammary gland image, which is present on a front side; that is, a shallow side, of the boundary image. The ROI is automatically set so as to cover the mammary gland image, on the basis of the boundary image. This will be described in more detail later.

A boundary smoothing unit 40 smooths a boundary point sequence including a plurality of boundary points or a lower side of the ROI based on the boundary point sequence. Since the boundary point sequence or the lower side is smoothed by this smoothing, in a case where the ROI is displayed, an appearance of the ROI is improved. In addition, this smoothing prevents or alleviates a phenomenon in which a form of the ROI becomes unnatural. This smoothing is a spatial smoothing. The boundary smoothing unit 40 according to the embodiment further has a function of smoothing the boundary point sequence or the lower side in a time axis direction. It is possible to suppress the form of ROI from being severely changed in units of frames by the temporal smoothing, such that it is possible to mitigate a feeling of eyesore. However, the temporal smoothing may not be conducted during a period in which the ultrasonic probe is being moved.

The ROI generating unit 42 functions as an ROI generation means, which determines the ROI on the basis of the boundary point sequence. Specifically, the lower side of the ROI is determined on the basis of the boundary point sequence. Two sides (left side and right side) of the ROI may be aligned with two sides of the tomographic image. The side may be constituted by a line generated by the smoothing. An upper side of the ROI coincides with an upper side of the tomographic image. However, the upper side of the ROI may be set at a position spaced apart from the upper side of the tomographic image. In any case, the ROI is generated so that the tissue that is an image analysis target is covered as much as possible. The ROI having a rectangular shape as a basic shape is generated, but an ROI having another shape may be generated. The image analyzing unit 24 cuts a partial image from the tomographic image or the like based on the generated ROI, and executes an analysis on the partial image. Alternatively, the image analyzing unit 24 defines an analysis target range in the tomographic image or the like based on the generated ROI, and executes an analysis within the analysis target range.

Figure 3:
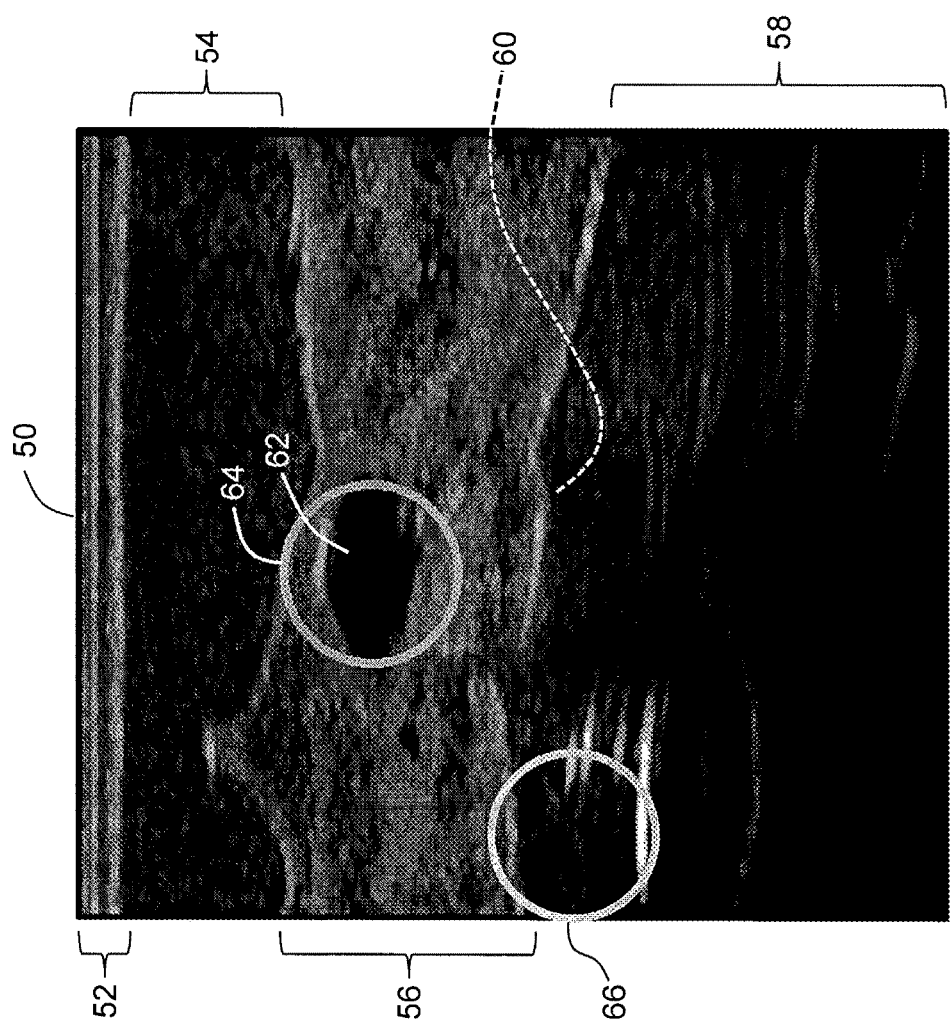
FIG. 3 is a view illustrating a comparative example.

FIG. 3 illustrates a comparative example. In this comparative example, an ROI is not set, and an entire tomographic image 50 is an analysis target. The tomographic image 50 includes a surface layer image 52, a fat layer image 54, a mammary gland image 56, and a greater pectoral muscle image 58. A boundary image 60 appears between the mammary gland image 56 and the greater pectoral muscle image 58. The boundary image 60 is an image that appears generally clearly. When an image analysis is executed on such a tomographic image 50, markers 64 and 66 as illustrated in FIG. 3 are automatically displayed. The marker 64 points to a low-luminance tumor 62. On the other hand, the marker 66 points to a low-luminance portion in the greater pectoral muscle; that is, erroneous recognition occurs. In the greater pectoral muscle image 58, a rib image may appear, and an artifact may also appear. The erroneous recognition is caused by such elements. A target that a user (a doctor, an examination technician, or the like) wishes to observe is a tumor or the like included in the mammary gland image 56, and the tumor or the like appears above the boundary image 60. On the other hand, a region having generally uniformity at a relatively low luminance spreads below the boundary image 60. Several peculiarities as described above are recognized in the tomographic image of the breast. In the embodiment, a region of interest is automatically and appropriately determined using such peculiarities. This will be described in detail below.

Figure 4:
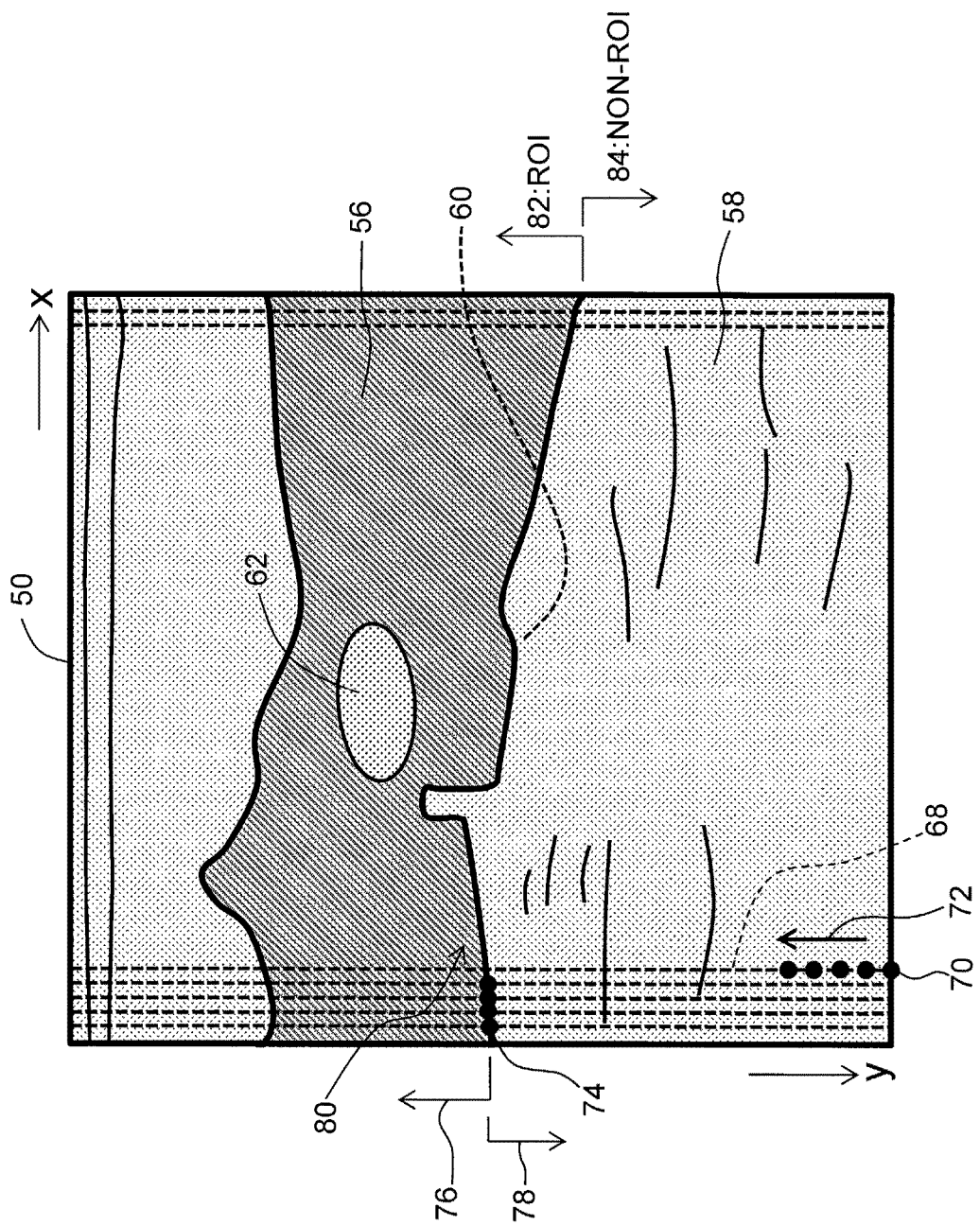
FIG. 4 is a view illustrating an ROI generating method according to an embodiment.

FIG. 4 illustrates a boundary image detecting method according to the embodiment. FIG. 4 is a schematic view corresponding to the tomographic image illustrated in FIG. 3. x indicates a horizontal direction (transverse direction), which is the electronic scanning direction in the embodiment. y indicates a vertical direction (longitudinal direction), which is the depth direction in the embodiment.

In the tomographic image, the boundary image 60 has a form in which the boundary image extends in a direction intersecting with the y direction, which is the depth direction, as a whole. A direction in which the boundary image 60 flows is generally in the x direction, but there are many cases where the direction in which the boundary image 60 flows is inclined with respect to the x direction.

In the embodiment, a plurality of search paths 68 are set for the tomographic image. The plurality of search paths 68 traverse a plurality of positions in the boundary image 60 flowing in the transverse direction. Specifically, each search path 68 corresponds to each vertical pixel column constituting the tomographic image. Most of all, the plurality of search paths 68 may be set while being separated from each other in the horizontal direction. A search along the search paths and a search in the transverse direction from boundary points may be used in combination. For example, a boundary search is sequentially executed in the search paths 68 from a first search path to a final search path. The plurality of search paths may be inclined with respect to the y direction. In convex scanning, search paths may be radially set parallel to each beam direction (depth), or search paths may be set parallel to the vertical direction in an image.

On each search path 68, in the illustrated example, the deepest coordinate is a start point 70 of the search. As denoted by reference numeral 72, the boundary search is repeatedly executed from the start point 70 toward a shallow side; that is, in a direction approaching the ultrasonic probe. Specifically, each echo data is used as attention data, and a determination is made as to whether or not a luminance condition is satisfied for each attention data. In a case where the luminance condition is satisfied, a coordinate of the attention data is recognized as a boundary point 74. The luminance condition is, for example, a condition in which a minimum value of luminance in a window centered on the attention data is equal to or more than a predetermined threshold value, as described below. The boundary point 74 in each search path 68 is a point on the boundary image 60, and at the same time, is a point separating from each other a portion 76 belonging to a region of interest and a portion 78 belonging to a non-region of interest. The start point may be a point shallower than the deepest point.

Finally, a boundary point sequence 80 including a plurality of boundary points 74 arranged along the boundary image 60 is formed. The boundary point sequence 80 corresponds to a lower side of the ROI. The lower side is a boundary line separating the ROI 80 and the non-ROI from each other. A case can occur where the boundary point cannot be detected depending on a local state of the image. A case where another point is erroneously recognized as the boundary point can occur. In order to prevent the erroneous recognition, it is desirable to combine other conditions with each other, in addition to the luminance condition.

Figure 5:
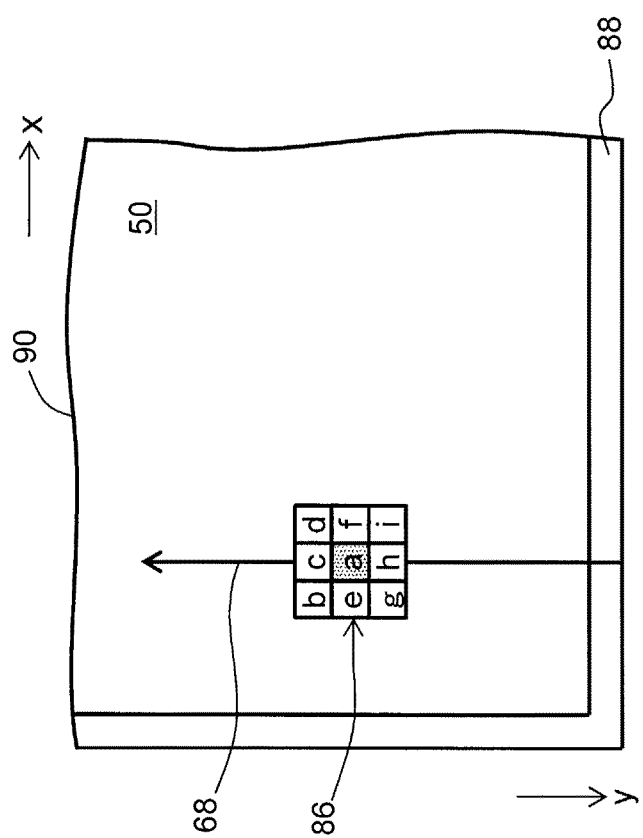
FIG. 5 is a view illustrating a boundary detecting method.

FIG. 5 illustrates an example of a boundary detecting method. A tomographic image is denoted by reference numeral 50, and a region 88 filled with zero value is present outside the tomographic image. Here, an image including the tomographic image 50 and the region 88 is a processing target image 90.

In the illustrated example, a window 86 is set for each data (attention data) a on a search path 68. The window 86 has a size of 3×3 (see a to i). For example, in a case where a minimum value of luminance in the window 86 is less than a threshold value, a non-boundary is determined, and in a case where the minimum value of the luminance in the window 86 is equal to or more than the threshold value, a boundary is determined. A coordinate of the attention data at a point in time when a luminance condition is satisfied is a boundary point. A point shallower than the coordinate or a point deeper than the coordinate based on the coordinate may be determined as the boundary point. In an inner portion of a greater pectoral muscle image, a minimum value of luminance is close to zero, whereas in a boundary image, a minimum value of luminance becomes large. The boundary is determined using such a difference. Instead of the minimum value of the luminance, an average value of luminance or the like may be used. In addition, a one-dimensional window may be used instead of a two-dimensional window. Alternatively, it may be the case that only the attention data is referred to. Alternatively, a histogram or the like may be created on the basis of a plurality of data in the window, and the boundary may be determined on the basis of the histogram or the like.

Figure 6:
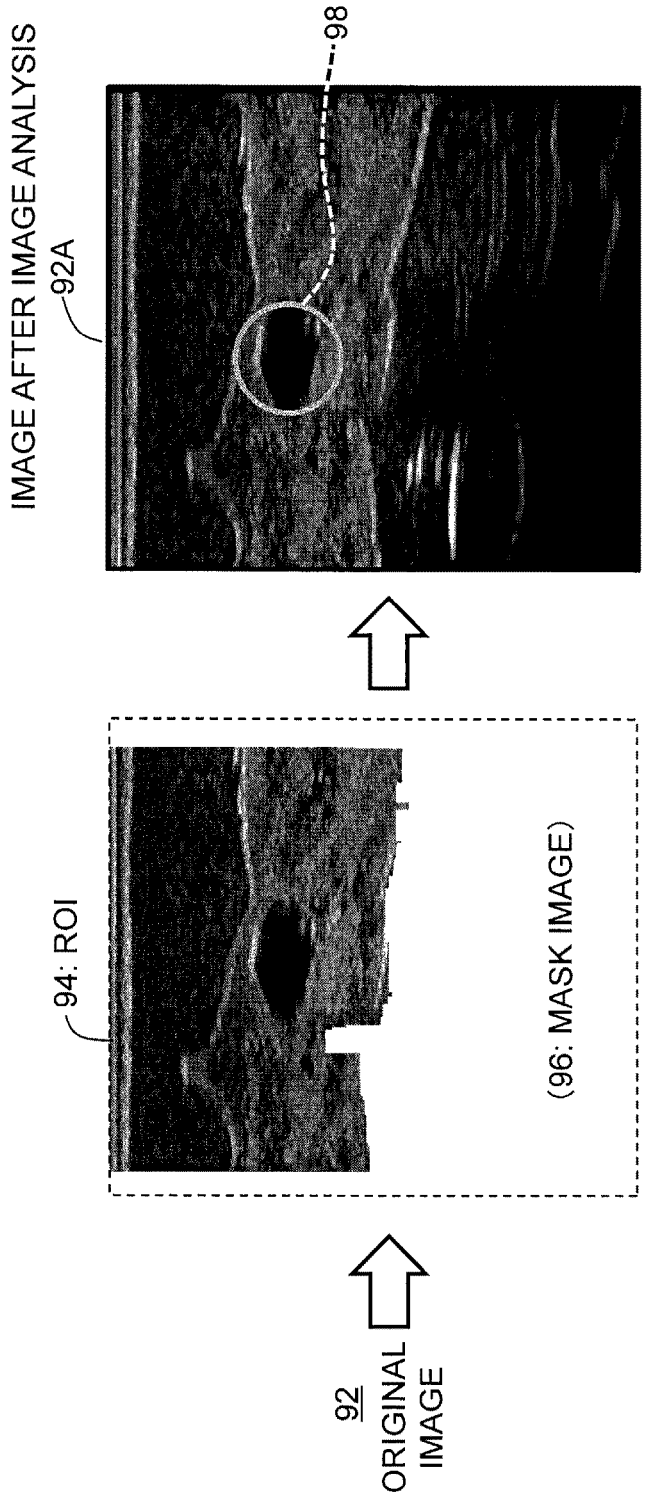
FIG. 6 is a view illustrating generation and application of an ROI.

In FIG. 6, an original image 92 is a tomographic image or is an image obtained by performing zero padding on the original image. An ROI 94 generated as described above is applied to the original image 92. An inner portion of the ROI 94 is an image analysis target. An outer portion of the ROI 94 is a mask region, and is represented as a mask image 96 in FIG. 6. An image showing an image analysis result is denoted by reference numeral 92A. In the image 92A of the image analysis result, a tumor image included in a mammary gland image is marked with a marker 98. A low-luminance portion is included in a greater pectoral muscle image, but a marker is not given to the low-luminance portion. That is, the erroneous recognition described in FIG. 3 is prevented.

Figure 7:
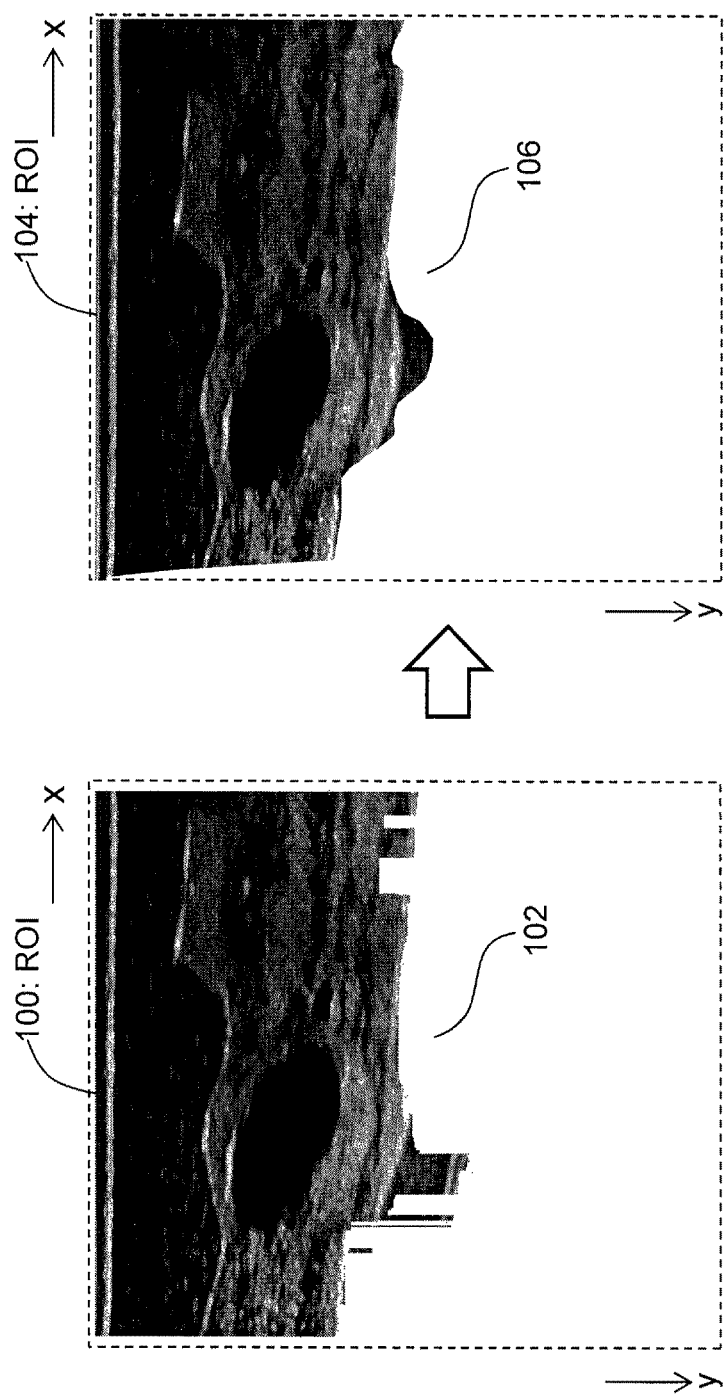
FIG. 7 is a view illustrating states before and after smoothing.

In FIG. 7, ROI images 100 and 104 before and after being smoothed respectively, are illustrated. The ROI image 100 has a lower side 102, which has a considerably complicated form. A form of a detection point sequence is reflected in a form of the lower side 102 as it is. A lower side 106 of the ROI image 104 is obtained by smoothing the lower side 102. The lower side 106 has a smooth shape as a whole. It should be noted that the lower side 106 of the ROI image 104 schematically or exaggeratedly illustrates a smoothing action and is not generated by actual smoothing processing.

Figure 8:
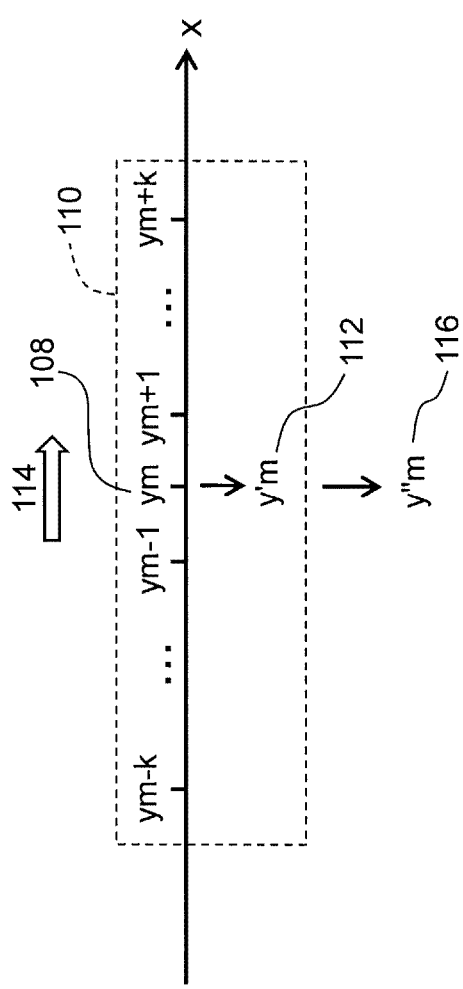
FIG. 8 is a view for describing smoothing on a time axis.

FIG. 8 illustrates a smoothing method. An x direction is a horizontal direction, and y coordinates of a plurality of boundary points detected on a plurality of search paths are shown on an x axis. Among them, y coordinates (ym−k to ym to ym+k) included in a predetermined section 110 centered on an attention x coordinate (y coordinate is ym) (see reference numeral 108) are specified, an average value y′m of the y coordinates is calculated (see reference numeral 112), and the average value y′m is given to the attention x coordinate. This processing is repeatedly executed while moving the section 110 (see reference numeral 114). Instead of a simple average, a weighted average or the like may be used. Further, in each x coordinate, the y coordinates may be smoothed in the time axis direction to calculate an average value y″m (see reference numeral 116), and the average value y″m may be given to each x coordinate. According to spatial smoothing, an appearance of the ROI can be improved in a frame, and according to temporal smoothing, the appearance can be improved between frames.

Figure 9:
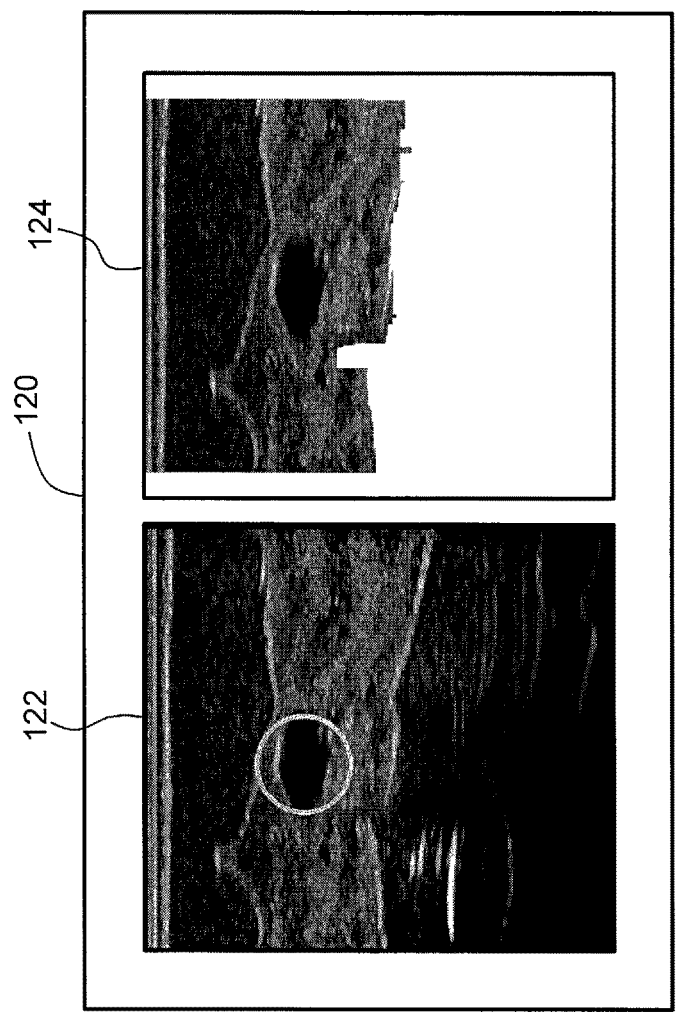
FIG. 9 is a view illustrating a display example.

FIG. 9 illustrates a display example. A display image 120 is constituted by an analysis result image 122 and an ROI image 124 arranged in a left and right direction, respectively. The analysis result image 122 is constituted by a tomographic image and a marker. The ROI image 124 is a reference image constituted by an image portion cut from the tomographic image. It is possible to confirm a portion that is an image analysis target through the ROI image 124. A graphic representing an ROI may be superimposed and displayed on the analysis result image 122.

Figure 10:
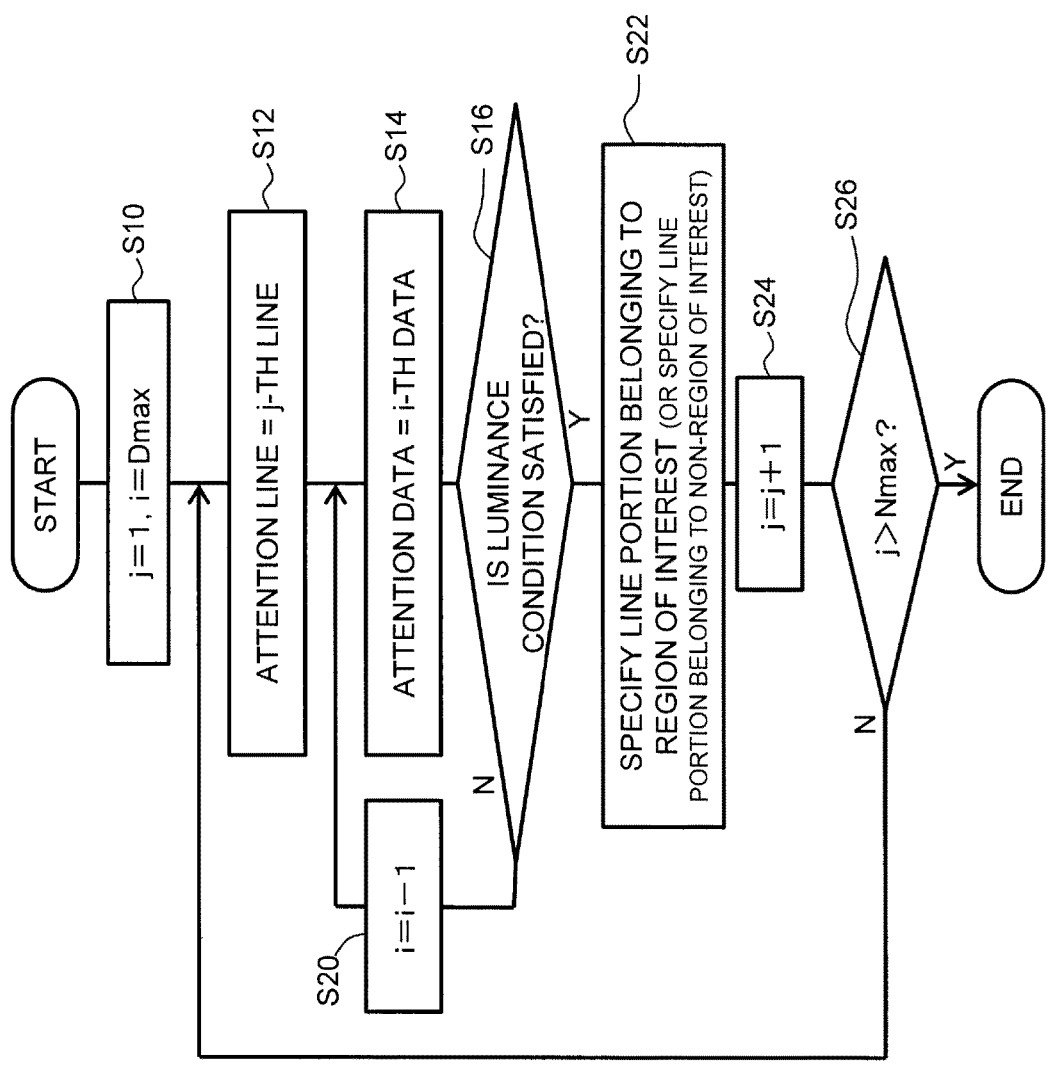
FIG. 10 is a view illustrating a first example of an ultrasonic image processing method.

FIG. 10 is a flowchart illustrating a first example of an ultrasonic image processing method according to the embodiment. This flowchart illustrates an operation of the image processing module included in the ultrasonic diagnostic apparatus illustrated in FIG. 1.

In S10, as an initial setting, 1 is given to j as a counter, and a maximum value Dmax is given to i as a counter. j indicates a line number (vertical pixel column number), and i indicates a depth number. In S12, an attention line as a boundary search path is a j-th line. In S14, attention data is i-th data. In S16, it is determined whether or not the above luminance condition is satisfied. In a case where the luminance condition is not satisfied, the processing proceeds to S20, and i is decremented by 1.

On the other hand, in a case where the luminance condition is satisfied in S16, a coordinate of the attention data is a boundary point, a line portion in front of the boundary point is a portion of a region of interest, and a line portion behind the boundary point is a portion of a non-region of interest, in S22. The boundary point itself may be any region. In S24, j is incremented by 1. In S26, it is determined whether or not j exceeds Nmax. Nmax is a maximum line number. When j does not exceed Nmax, each step from S12 is repeatedly executed. When j exceeds Nmax, the present processing ends.

Figure 11:
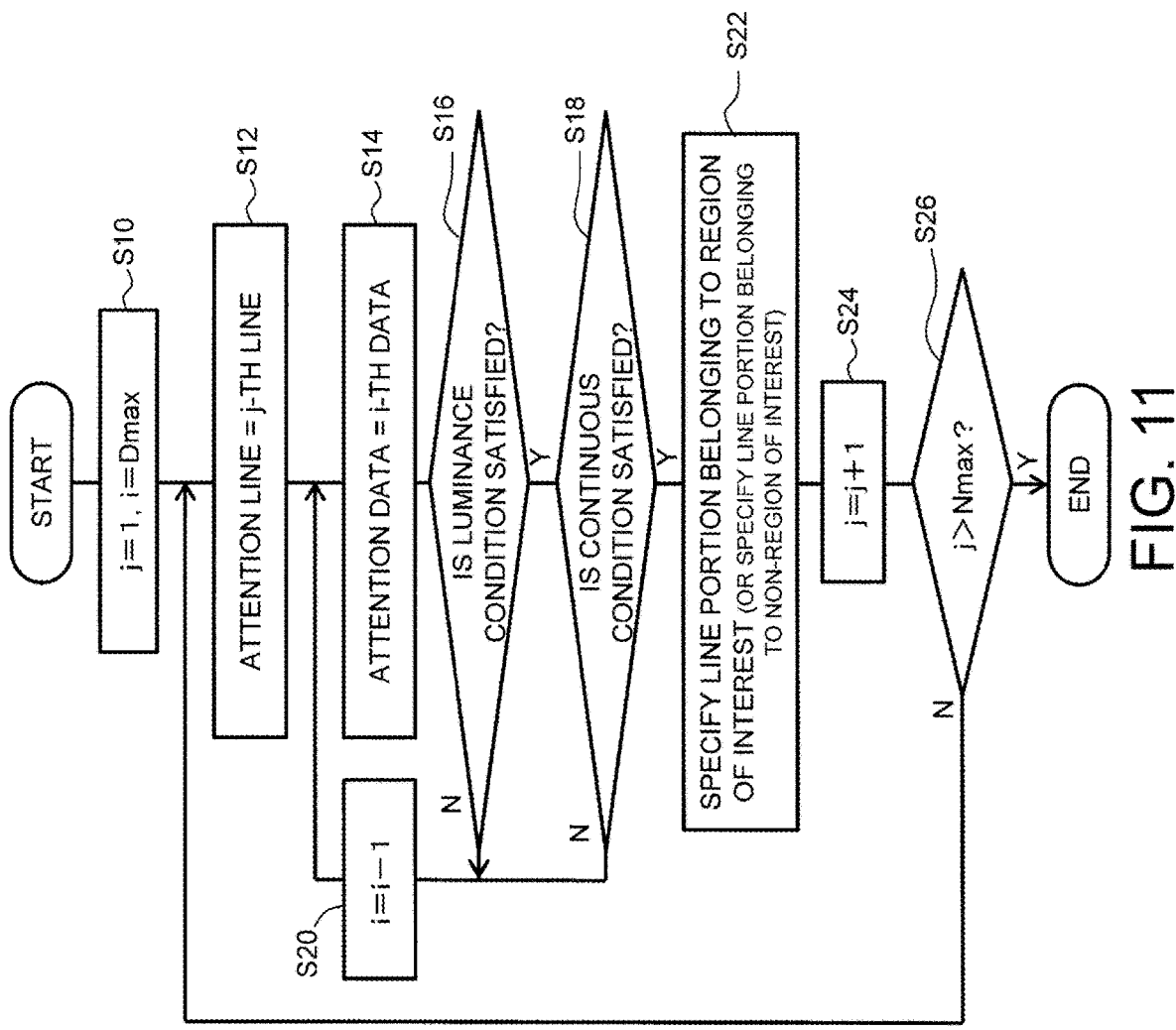
FIG. 11 is a view illustrating a second example of an ultrasonic image processing method.

FIG. 11 is a flowchart illustrating a second example of an ultrasonic image processing method according to the embodiment. The same steps as those illustrated in FIG. 11 are denoted by the same step numbers, and a description thereof is omitted.

In this second example, S18 is provided after S16. In S18, it is determined whether or not the luminance condition is continuously satisfied n times. That is, it is determined whether or not a continuous condition is satisfied. In a case where the continuous condition is not satisfied, the processing proceeds to S20, and in a case where the continuous condition is satisfied, the processing proceeds to S22. In an inner portion of a greater pectoral muscle image, a horizontal stripe-shaped image is generated, but a thickness of the horizontal stripe-shaped image in a vertical direction is small, and it is difficult to satisfy the continuous condition. On the other hand, a boundary image has a predetermined thickness in a depth direction, and many high-luminance pixels are present in an inner portion of the boundary image. Therefore, in a case where a boundary search proceeds into a mammary gland image, it is easy to satisfy the continuous condition. According to the second example, it is possible to more accurately detect the boundary image. n is an integer of 1 or more. n may be variably set adaptively depending on a diagnostic range (diagnostic depth range).

Figure 12:
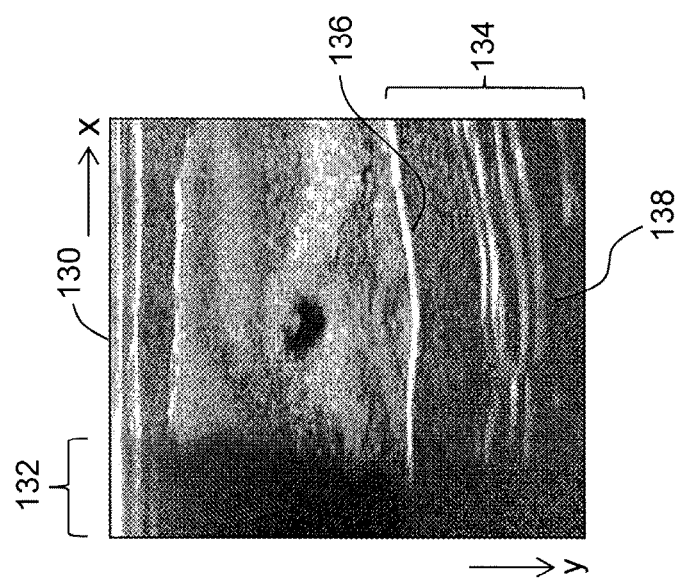
FIG. 12 is a view illustrating a tomographic image including a shadow and a costal image.

An effect of the second example will be described with reference to FIGS. 12 to 14. FIG. 12 illustrates a tomographic image 130 of the breast. The tomographic image 130 includes a boundary image 136 and a greater pectoral muscle image 134, and a rib image 138 is recognized in the greater pectoral muscle image 134. In addition, a shadow 132 is generated at a left end portion of the tomographic image 130. For example, in a case where an end portion of the transmission and reception surface of the ultrasonic probe is apart from a body surface, or adhesion between the end portion of the transmission and reception surface of the ultrasonic probe and the body surface is decreased, it is easy for such a shadow to be generated.

FIG. 13 illustrates a processing result of the first example. Here, a non-ROI (mask region) 140 is indicated by a broken line. The rest portion corresponds to an ROI. Most of the shadow is incorporated in the non-ROI 140, such that the shadow being an analysis target is avoided. However, an end portion of the boundary image enters the shadow while having a low luminance, and is detected as a boundary, such that a portion of the shadow is out of the non-ROI 140 to enter the ROI. In addition, an upper side 140*a* of the non-ROI 140 corresponding to a lower side of the ROI is set along the rib image 138, such that erroneous detection occurs.

FIG. 14 illustrates a processing result of the second example. In the second example, the continuous condition is added, and a form of a non-ROI 142 is thus valid. That is, an upper side 142*a* is set along a portion of the boundary image 136 excluding an end portion, and the upper side 142*a* is not influenced by the rib image 138. As described above, according to the second example, it is possible more accurately set the ROI.

In FIG. 15, a boundary determining method based on a tomographic image is summarized. Here, a luminance condition 144, a space (continuous) condition 158, and a time (continuous) condition 160 are illustrated. Each of the conditions 144, 158, and 160 can be used alone, or they can be used in combination with each other.

Upon application of the luminance condition 144, a minimum value 145, an average value 146, another representative value 148, and the like, within a window can be referred to. Alternatively, a histogram 150 based on luminance or another characteristic amount 152 within the window may be referred to. One or a plurality of reference values are compared with one or a plurality of threshold values 156 to determine whether or not the luminance condition is satisfied (see reference numeral 154). The space condition 158 is a condition for evaluating spatial continuity. For example, in a case in which one or a plurality of detection points detected up to the current time are not far apart from each other in a vertical direction, it is determined that the space condition 158 is satisfied for the one or the plurality of detection points. The time condition 160 is a condition for evaluating temporal continuity. For example, in a case in which one or a plurality of detection points arranged on a time axis and detected in the past are not far apart from each other in the vertical direction, it is determined that the time condition is satisfied for the one or the plurality of detection points. In a case where one or a plurality of the conditions 144, 158, 160 are satisfied, a boundary is determined (see reference numeral 162).

The tomographic image of the breast is the processing target in the above embodiment, but another tomographic image or another ultrasonic image may be the processing target. For example, a tomographic image of the abdominal organ may include a boundary image flowing in a transverse direction and a low-luminance region below the boundary image. The above processing may be applied to such an image. The image analysis target is defined by the region of interest in the above embodiment, but the region of interest may be used for other purposes. For example, a range in which the elastography image is created may be automatically set as the region of interest.

The invention claimed is:

1. An ultrasonic diagnostic apparatus comprising:
   a detecting unit that detects a plurality of boundary points by setting a plurality of search paths so as to traverse a plurality of positions in a boundary image on an ultrasonic image including the boundary image and performing a boundary search from a deep spot to a shallow spot on the plurality of search paths, the boundary image having a form which extends in a direction intersecting with a depth direction; and a generating unit that generates a region of interest including an attention tissue image present on a shallow side of the boundary image on the basis of the plurality of boundary points.

2. The ultrasonic diagnostic apparatus according to claim 1,
wherein the attention tissue image is a mammary gland image, and
the boundary image is a boundary image between the mammary gland image and a greater pectoral muscle image present at a spot deeper than that of the mammary gland image.

3. The ultrasonic diagnostic apparatus according to claim 1,
wherein the region of interest defines a portion that is an analysis target in the ultrasonic image or another ultrasonic image.

4. The ultrasonic diagnostic apparatus according to claim 1,
wherein a lower side of the region of interest is determined on the basis of a boundary point sequence including the plurality of boundary points, and
a smoothing unit that spatially smooths the lower side is provided.

5. The ultrasonic diagnostic apparatus according to claim 4,
wherein the smoothing unit further smooths the spatially smoothed lower side temporally.

6. The ultrasonic diagnostic apparatus according to claim 1,
wherein the detecting unit detects each of the boundary points on the basis of satisfaction of a luminance condition on each of the search paths.

7. The ultrasonic diagnostic apparatus according to claim 6,
wherein the detecting unit detects each of the boundary points on the basis of continuous satisfaction of the luminance condition on each of the search paths.

8. The ultrasonic diagnostic apparatus according to claim 7,
wherein the detecting unit detects each of the boundary points on the basis of continuous satisfaction of the luminance condition n times on each of the search paths, and
the value n is adaptively set on the basis of a diagnostic range.

9. The ultrasonic diagnostic apparatus according to claim 1, further comprising
a display unit that displays a region-of-interest image showing the region of interest together with the ultrasonic image.

10. An ultrasonic image processing method comprising:
a generating step of generating a region of interest including an attention tissue image present on a shallow side of a boundary image on the basis of the boundary image, the boundary image having a form which extends in a direction intersecting with a depth direction on an ultrasonic image; and
a displaying step of displaying an image representing the region of interest together with an image representing a result of an analysis performed on an image portion in the region of interest in the ultrasonic image or another ultrasonic image,
wherein in the generating step, a boundary search from a deep spot to a shallow spot on the ultrasonic image is executed, and the region of interest is determined on the basis of a result of the boundary search.

11. A program executed in an ultrasonic image processing apparatus, comprising
a function of detecting a plurality of boundary points by setting a plurality of search paths so as to traverse a plurality of positions in a boundary image on an ultrasonic image including the boundary image and performing a boundary search from a deep spot to a shallow spot on the plurality of search paths, the boundary image having a form which extends in a direction intersecting with a depth direction; and
a function of generating a region of interest including an attention tissue image present on a shallow side of the boundary image on the basis of the plurality of boundary points.

* * * * *